(12) United States Patent
Mio et al.

(10) Patent No.: US 12,233,025 B2
(45) Date of Patent: Feb. 25, 2025

(54) PLASTIC CONTAINER

(71) Applicant: Fujimori Kogyo Co., Ltd., Tokyo (JP)

(72) Inventors: Atsushi Mio, Tokyo (JP); Toyoaki Suzuki, Tokyo (JP); Junpei Nomura, Tokyo (JP); Kaho Toyabe, Tokyo (JP)

(73) Assignee: ZACROS Corporation, Tokyo (JP)

( * ) Notice: Subject to any disclaimer, the term of this patent is extended or adjusted under 35 U.S.C. 154(b) by 1152 days.

(21) Appl. No.: 16/969,903

(22) PCT Filed: Feb. 13, 2019

(86) PCT No.: PCT/JP2019/005106
§ 371 (c)(1),
(2) Date: Aug. 13, 2020

(87) PCT Pub. No.: WO2019/159967
PCT Pub. Date: Aug. 22, 2019

(65) Prior Publication Data
US 2021/0007930 A1     Jan. 14, 2021

(30) Foreign Application Priority Data

Feb. 15, 2018  (JP) .................................. 2018-024825

(51) Int. Cl.
*A61J 1/10*     (2006.01)
*A61J 1/14*     (2023.01)
(Continued)

(52) U.S. Cl.
CPC .............. *A61J 1/10* (2013.01); *A61J 1/1468* (2015.05); *A61J 1/1475* (2013.01); *A61L 31/06* (2013.01); *A61L 31/14* (2013.01); *C07D 231/26* (2013.01)

(58) Field of Classification Search
CPC ...... A61J 1/2013; A61J 1/1475; A61J 1/1468; A61J 1/14; A61J 1/10; C07D 231/26; A61L 31/028; A61L 31/14; A61L 31/06
(Continued)

(56) References Cited

U.S. PATENT DOCUMENTS 8,622,213 B2 *  1/2014  Lynn .................... B31B 70/844
                                                      604/408
9,101,532 B2 *  8/2015  Hiranuma ............. A61J 1/2093
(Continued)

FOREIGN PATENT DOCUMENTS

CN        101917991 A     12/2010
CN        103282199 A      9/2013
(Continued)

OTHER PUBLICATIONS

European Search Report dated Dec. 14, 2021 in related EP Application No. 1975448.6.
(Continued)

*Primary Examiner* — Anthony D Stashick
*Assistant Examiner* — Raven Collins
(74) *Attorney, Agent, or Firm* — Harris Beach Murtha Cullina, PLLC (57) ABSTRACT

A plastic container has superior storage stability for pharmaceutical ingredients exhibiting a high affinity to plastic and can be mass-produced at low cost. The container has a bag body formed into a bag shape by a sheet member with a storage part on the inside thereof, and a tubular port member attached to the bag body, wherein one end of the tubular port member communicates with the storage part and an opening part of the other end is exposed outside of the bag body. The sheet member is formed from two or more layers including a base resin layer and an innermost layer formed from an amorphous polymer, as a main component, formed by polymerizing at least one type of olefin monomer, having a cyclic hydrocarbon skeleton, and the port member is formed from a resin having a crystalline polyolefin having no cyclic hydrocarbon skeleton, as a main component.

18 Claims, 1 Drawing Sheet

(51) Int. Cl.
   *A61L 31/06* (2006.01)
   *A61L 31/14* (2006.01)
   *C07D 231/26* (2006.01)
(58) Field of Classification Search
   USPC .......................... 206/438; 604/403, 408, 409
   See application file for complete search history.

(56) References Cited

U.S. PATENT DOCUMENTS

2010/0163446 A1* 7/2010 Suzuki ................ B32B 27/325
                                                          428/35.4
2010/0320215 A1   12/2010 Ozaki et al.

FOREIGN PATENT DOCUMENTS

| EP | 2226059 A1 * | 9/2010 | ................ A61J 1/10 |
|----|-------------|--------|---------|
| JP | 5184642 A | 7/1993 | |
| JP | 2002528177 A | 9/2002 | |
| JP | 200818063 A | 1/2008 | |
| JP | 2010081971 A | 4/2010 | |
| JP | 201457723 A | 4/2014 | |
| WO | 0024357 A | 5/2000 | |
| WO | 2009066752 A1 | 5/2009 | |

OTHER PUBLICATIONS

National Intellectual Property Administration, PRC Office Action for Application No. 201980013493.3 dated Nov. 21, 2022.
National Intellectual Property Administration, PRC Search Report for Application No. 201980012493 dated Nov. 21, 2022.

* cited by examiner

PLASTIC CONTAINER

FIELD OF THE INVENTION

The present invention relates to a plastic container having superior storage stability of a pharmaceutical product, and in particular, a pharmaceutical formulation having a high affinity with plastics. More specifically, the present invention relates to a plastic container in which an innermost layer of a sheet member forming a bag body of a bag is formed from an amorphous polymer, as a main component, by polymerizing at least one type or two or more types of olefin monomers, in which at least one type among the olefin monomers is a monomer having a cyclic hydrocarbon skeleton, and a port member forming an opening part is formed from a crystalline polyolefin having no cyclic hydrocarbon skeleton, as a main component.

Priority is claimed on Japanese Patent Application No. 2018-024825, filed on Feb. 15, 2018, in Japan, the content of which is incorporated herein by reference.

BACKGROUND OF THE INVENTION

In recent years, a soft bag for a formulation has been developed, in which an injectable pharmaceutical agent is diluted in advance, and prepared as a formulation for intravenous infusion and filled in a flexible container (plastic container) made of plastic or the like. Such a soft bag contained with a formulation is deemed to be useful because of reducibility of the risk of breakage and superior disposability, as compared to those of glass bottles and ampules, in addition to convenience and rapidity at the time of use.

However, it is known that in some pharmaceutical products including radical scavenging formulations, adsorption or absorption (such a physiochemical behavior may be referred to as "sorption" in some cases) on or permeation to a film formed from a common crystalline polyolefin-based resin such as polyethylene (hereinafter sometimes referred to as "PE") or polypropylene (hereinafter sometimes referred to as "PP"), or a resin commonly used as a material for a container of a pharmaceutical product, such as vinyl chloride, may occur. This is a problem in developing a soft bag contained with a formulation, such that sufficient stability cannot be obtained due to the interaction between the ingredients of the pharmaceutical solution and the plastic container.

Therefore, it has been proposed to use a cyclic polyolefin-based resin as a resin having no sorption or no permeation with respect to pharmaceutical products and the like in a plastic container.

For example, Patent Document 1 (Japanese Unexamined Patent Application, First Publication No. 2008-18063) proposes a multilayer body in which a cyclic polyolefin resin layer is disposed as an innermost layer, and an intermediate layer and an outermost layer are formed from a PE-based resin. In the plastic container obtained in the Example of Patent Document 1, a bag body formed from the multilayer body which is the same invention as the pharmaceutical container is connected to a mouth part formed from a cyclic polyolefin resin. However, it is not preferable to use a cyclic polyolefin-based resin, which is generally used as a pharmaceutical container and is more expensive as compared with a PE-based resin or a PP-based resin, as a material for the port member in view of not only a material cost, but also relatively reduced productivity due to increase of the period for welding between the sheet member and the port member. For this reason, this is not preferable in terms of cost. In addition, after sealing the mouth part with a rubber plug or the like, it is necessary to maintain a sealing property by means of a cap. However, in order to exhibit sufficient strength at the joint part, the cap member must also be formed from a cyclic olefin-based resin. In this point of view, there is also a problem of cost.

In addition, Patent Document 2 (PCT International Publication No. 2009/066752) discloses an example in which a bag container is formed from a multilayer sheet in which an innermost layer is made of a PP-based resin, an intermediate layer is made of a cyclic polyolefin-based resin, and an outermost layer is made of a PP-based resin. The example of Patent Document 2 describes that an aqueous solution of edaravone is contained as contents, and describes change in the amount of the ingredient before and after sterilization for 30 minutes at 115° C. In this case, it is indicated that content reduction due to the sterilization treatment is suppressed as compared with a bag container formed only from a PP-based resin, but sorption of the contents to the PP-based resin layer directly contacting with the contents is unavoidable, and has a problem in that a further decrease in contents may be caused during storage for a long period of time after sterilization.

As described above, in a container for containing a pharmaceutical product having an ingredient with a high affinity for plastic, a form that can be provided at low cost while having sufficient storage stability as a pharmaceutical application has not been realized. The development of such a container is desired.

SUMMARY OF THE INVENTION

Technical Problem

The present invention has been completed in view of the circumstances mentioned above. An object of the present invention is to provide a plastic container which has superior storage stability with respect to a pharmaceutical ingredient exhibiting a high affinity for plastic and can be mass-produced at low cost.

Solution to Problem

In order to solve the above problems, the inventors of the present application focused on the relationship between a ratio of a content contact area of a sheet member forming the plastic container and a content contact area of a port member, and the volume of the contents to be stored, and discovered that by forming the sheet member constituting a bag body portion from a laminate including an innermost layer formed from a specific resin component, and using a material composition mainly composed of a crystalline polyolefin resin as the port member, the contents of which are stored in the plastic container can be stably stored even during a sterilization process. Thereby, the present invention was completed.

In the plastic container of the present invention, with respect to the material constituting the bag container, the innermost layer of the sheet member is formed from an amorphous polymer, as a main component, which is formed by polymerizing at least one type or two or more types of olefin monomers, in which at least one type of the olefin monomers is a monomer having a cyclic hydrocarbon skeleton, and the port member is formed from a crystalline polyolefin having no cyclic hydrocarbon skeleton, as a main component. When an aqueous solution containing a pyrazolone derivative or a pharmaceutically acceptable salt thereof as contents, is stored in a storage part of the plastic container of the present invention, stable storage is possible during heat sterilization and even during subsequent static storage. Therefore, it can be seen that a soft bag for a formulation producible at low cost can be obtained.

The plastic container of the present invention is characterized by possessing a bag body which is formed into a bag shape by a sheet member and has a storage part on the inside thereof, and a tubular port member attached to the bag body, in which one end of the tubular port member communicates with the storage part and an opening part of the other end is exposed outside of the bag body, wherein the sheet member mentioned above is formed from two or more layers including a base resin layer and an innermost layer, the innermost layer mentioned above is mainly formed from an amorphous polymer formed by polymerizing at least one type or two or more types of olefin monomers, in which at least one type of the olefin monomers is a monomer having a cyclic hydrocarbon skeleton, and the port member mentioned above is formed from a rein having a crystalline polyolefin having no cyclic hydrocarbon skeleton, as a main component.

The relationship between a content contact area $S_B$ (cm$^2$) of the bag body and a content contact area $S_P$ (cm$^2$) of the port member preferably satisfies the following (Expression 1).

$$0.01 \leq S_P/S_B \leq 0.15 \quad \text{(Expression 1)}$$

The crystalline polyolefin mentioned above may be selected from one or more types of polyethylene, polypropylene, and ethylene/alpha-olefin copolymer.

The amorphous polymer mentioned above may have a glass transition temperature of 70° C. or higher.

The amorphous polymer may have a glass transition temperature of 100° C. or higher.

The plastic container mentioned above may be in the form of an infusion bag or a blow molded container.

The contents stored in the plastic container may be a pharmaceutical product.

The pharmaceutical product mentioned above may be an aqueous solution containing a pyrazolone derivative or a pharmaceutically acceptable salt thereof.

The pyrazolone derivative mentioned above may be 3-methyl-1-phenyl-2-pyrazolin-5-one.

The plastic container of the present invention is also housed in a package having a gas barrier property together with an oxygen scavenger, as a preferable mode, from the viewpoint of storage stability of a pharmaceutical solution.

Advantageous Effects of the Invention

According to the present invention, a plastic container having superior storage stability of an aqueous solution which contains a pharmaceutical ingredient having a high affinity for plastic can be provided at low cost.

DETAILED DESCRIPTION OF THE INVENTION

Hereinafter, the present invention is described based on suitable embodiments.

As a typical example of a pharmaceutical ingredient having a high affinity with a plastic described in the embodiments, a pyrazolone derivative may be mentioned. As the pyrazolone derivative, a compound represented by the following Formula (I) can be used.

[Formula (I)]

In Formula (I), R$^1$ may represent a hydrogen atom, aryl, alkyl having 1 to 5 carbon atoms or alkoxycarbonyl alkyl having 3 to 6 carbon atoms in total, and R$^2$ may represent a hydrogen atom, aryloxy, aryl mercapto, alkyl having 1 to 5 carbon atoms, or hydroxyalkyl having 1 to 3 carbon atoms. Alternatively, R$^1$ and R$^2$ may combine to represent an alkylene having 3 to 5 carbon atoms.

In Formula (I), R$^3$ may be a hydrogen atom, alkyl having 1 to 5 carbon atoms, cycloalkyl having 5 to 7 carbon atoms, hydroxyalkyl having 1 to 3 carbon atoms, benzyl, naphthyl, phenyl, or phenyl substituted by 1 to 3 substituents which are the same or different (and selected from the group consisting of alkoxy having 1 to 5 carbon atoms, hydroxyalkyl having 1 to 3 carbon atoms, alkoxycarbonyl having 2 to 5 carbon atoms, alkyl mercapto having 1 to 3 carbon atoms, alkylamino having 1 to 4 carbon atoms, dialkylamino having 2 to 8 carbon atoms, halogen atom, trifluoromethyl, carboxyl, cyano, hydroxyl group, nitro, amino, and acetamide).

In addition to the compound represented by Formula (I), a pharmaceutically acceptable salt thereof can also be used. As examples of pharmaceutically acceptable salts, mention may be made of salts with mineral acids such as hydrochloric acid, sulfuric acid, hydrobromide, phosphoric acid, and the like; salts with organic acids such as methanesulfonic acid, p-toluenesulfonic acid, acetic acid, oxalic acid, citric acid, malic acid, fumaric acid, and the like; salts with alkali metals such as sodium, potassium, and the like; salts with alkaline earth metals such as magnesium, and the like; and salts with amines such as ammonia, ethanolamine, 2-amino-2-methyl-1-propanol, and the like. In addition thereto, the types of the salts are not particularly limited as long as they are pharmaceutically acceptable.

In addition to the pyrazolone derivative represented by Formula (I) or a pharmaceutically acceptable salt thereof, a hydrate or solvate thereof can also be used as an active ingredient of a pharmaceutical solution.

All the compounds represented by Formula (I) are known compounds, and can be easily synthesized by a person having ordinary skill in the art by a method described in Japanese Examined Patent Application, Second Publication No. H05-31523 (Examples of pharmaceutical products containing 3-methyl-1-phenyl-2-pyrazolin-5-one or a pharmaceutically acceptable salt thereof). In the case of 3-methyl-1-phenyl-2-pyrazolin-5-one (edaravone), R$^1$ is methyl, R$^2$ is a hydrogen atom, and R$^3$ is phenyl.

An aqueous solution containing the pyrazolone derivative represented by Formula (I) or a pharmaceutically acceptable salt thereof, or a hydrate or solvate thereof as an active ingredient, stored in the plastic container of the present embodiment can be prepared by dissolving the pyrazolone derivative in a solvent (for example, an infusion solution, or the like), adjusting the pH by adding a pH adjusting agent as desired, and adding other additives as desired so that the concentration of the pyrazolone derivative is about 0.06 mg/mL or more and about 2 mg/mL or less, and preferably about 0.3 mg/mL or more and about 0.6 mg/mL or less, for example, in the case of a formulation contained in a infusion bag.

The chemical solution used for preparing the aqueous solution containing the pyrazolone derivative is not limited as long as it is generally used as a pharmaceutical solution. As examples thereof, mention may be made of solutions prepared by dissolving one type or two or more types arbitrarily selected from electrolytes, saccharides, vitamins, proteins, and amino acids in water (for example, distilled water for injection) at an arbitrary concentration. In addition, a solution in which an electrolyte is dissolved may be referred to as an electrolyte solution, and a solution in which a saccharide is dissolved may be referred to as a sugar solution, in some cases. As examples of electrolytes, for example, sodium chloride and the like may be mentioned. These optional components can be used alone or in combination at any concentration. In the present embodiment, as a preferable chemical solution, for example, a solution prepared by dissolving, for example, sodium chloride or the like in water (for example, distilled water for injection or the like) at an arbitrary concentration. With respect to the amount of these substances the case of sodium chloride, for example, an amount equal to that of physiological saline, that is, 0.9% (WN) or the like is preferable.

The pH adjuster used for preparing an aqueous solution containing the pyrazolone derivative is not particularly limited as long as it is generally used as a pH adjuster for injections. In addition, the liquidity of the aqueous solution containing the pyrazolone derivative, that is, the pH, can be arbitrarily adjusted by using the pH adjuster described above.

Other additives used for preparing an aqueous solution containing the pyrazolone derivative are not particularly limited as long as they are generally used as additives for injections. In the present embodiment, as preferable other additives, mention may be made of, for example, pharmaceutical additives as described in "Japanese Pharmaceutical Excipients Dictionary" published by Yakuji Nippo, Limited, in 2000 (edited by the Japan Pharmaceutical Excipients Council). These additives may be added as a salt (for example, a monovalent alkali metal salt such as a sodium salt or a potassium salt) or may be added as a hydrate as desired. These additives are generally blended in a proportion usually used for injections. It is easily carried out by a person having ordinary skill in the art. In addition, as described in "Japanese Pharmaceutical Excipients Dictionary" published by Yakuji Nippo, Limited., in 2000 (edited by the Japan Pharmaceutical Excipients Council), these additives may be properly used depending on the purpose of use, for example, as stabilizers, surfactants, buffers, solubilizers, antioxidants, antifoamers, tonicity agents, emulsifiers, suspending agents, preservatives, soothing agents, solubilizers, solubilizing adjuvants, and the like. These additives can be added to an aqueous solution containing the pyrazolone derivative of the present embodiment or other pharmaceutical products, in combination of two or more types as desired.

In the case where the pH adjusters and other additives described above are used for the pharmaceutical product which is the contents of the present embodiment, the adding operations and mixing operations for the preparation of the aqueous solution can be performed according to ordinary pharmaceutical methods. For example, when preparing an aqueous solution containing only a pyrazolone derivative and a pH adjuster, the pyrazolone derivative and the pH adjuster may be respectively weighed and mixed, and then dissolved in water, or the weighed pH adjuster may be dissolved in an aqueous solution containing a pyrazolone derivative. Alternatively, a weighed pyrazolone derivative may be dissolved in an aqueous solution containing a pH adjuster. It is also possible to respectively prepare an aqueous solution containing a pH adjuster and an aqueous solution containing a pyrazolone derivative, and then mix these aqueous solutions so that the concentration of the pyrazolone derivative reaches the concentration mentioned above. In addition, when other additives are included, preparation can be carried out in the same manner as that described above.

Figure 1:
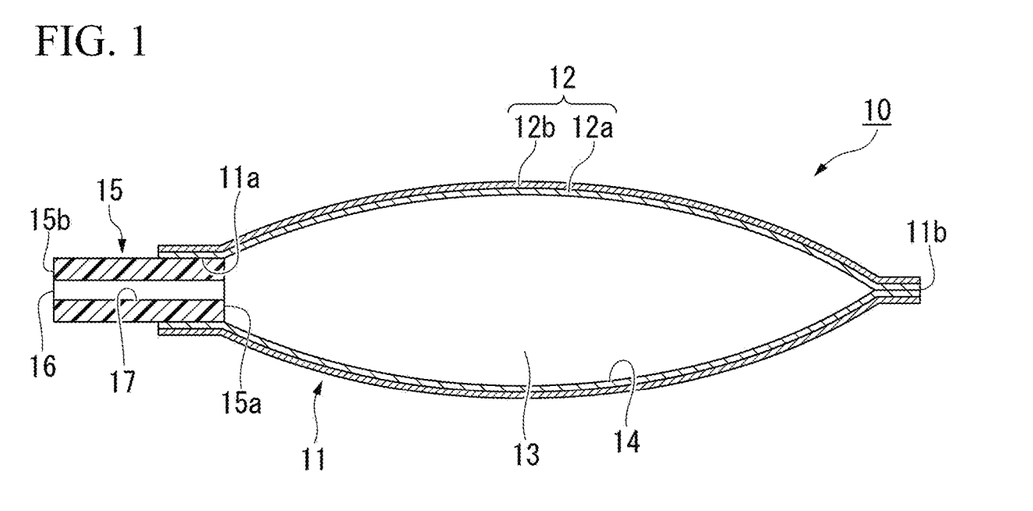
FIG. 1 is a cross-sectional view which shows a schematic structure of a plastic container of the present invention.
Figure 2:
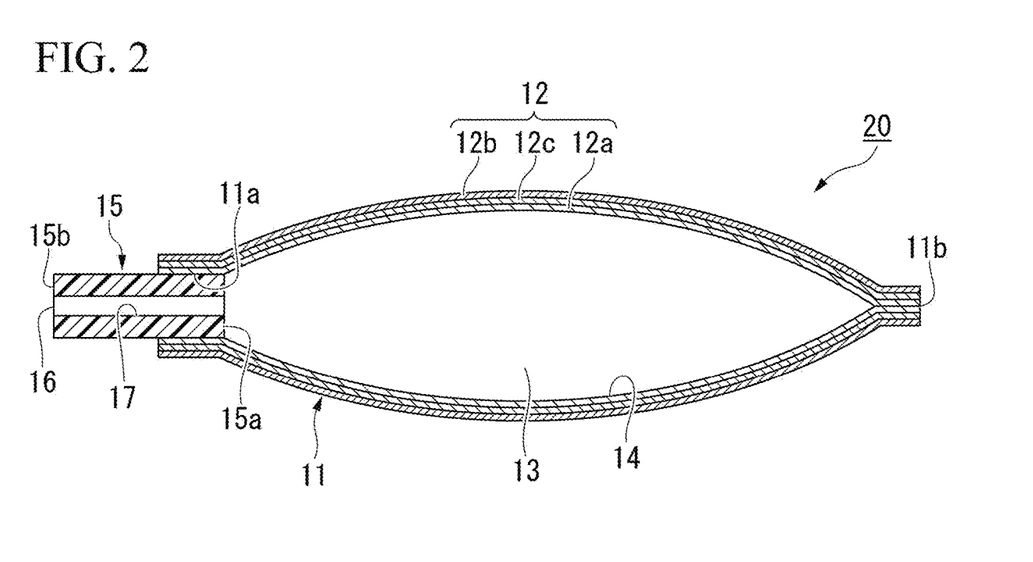
FIG. 2 is a cross-sectional view which shows an example of a plastic container of the present invention which has an adhesive resin layer.

The plastic container of the present embodiment possesses, as illustrated in FIG. 1 or FIG. 2, a bag body 11 which is formed into a bag shape by a sheet member 12 and has a storage part 13 on the inside thereof, and a tubular port member 15 attached to the bag body 11, in which one end 15*a* of the tubular port member communicates with the storage part 13 and an opening part 16 of the other end 15*b* is exposed outside of the bag body 11. The sheet member 12 is formed from two or more layers including a base resin layer 12*b* and an innermost layer 12*a*. The innermost layer 12*a* is mainly formed from an amorphous polymer formed by polymerizing at least one type or two or more types of olefin monomers, in which at least one type of the olefin monomers mentioned above is a monomer having a cyclic hydrocarbon skeleton, and the port member 15 is formed from a resin having a crystalline polyolefin having no cyclic hydrocarbon skeleton, as a main component.

In the present embodiment, the "main component" in each layer of the sheet member and the port member means that the ratio of the focused component to the entire matrix including the component exceeds 50% by mass.

The plastic container according to the present embodiment can be manufactured by using a sheet member including at least a base resin layer and an innermost layer in this order, superimposing the sheet members so that the innermost layer is placed as an inner surface, sealing the periphery thereof, and molding it together with a port member formed from a crystalline polyolefin resin, into a bag shape.

The thickness of the sheet member mentioned above is not particularly limited, but preferably ranges from 70 to 400 µm, and more preferably ranges from 150 to 300 µm from the viewpoint of strength and flexibility required as a container. The peripheral seal width is not particularly limited, but ranges from 2 to 20 mm, and preferably ranges from 3 to 7 mm.

In the sheet member, the innermost layer, which is a sealant layer mainly composed of an amorphous polymer, has a thickness ranging from 10 to 100 µm, and more preferably ranging from 20 to 80 µm. If the thickness of the innermost layer is less than 10 µm, the sealing performance may be insufficient, or the welding strength with the mouth part provided as necessary may be insufficient. In addition, when the mouth part is welded, the innermost layer is thinned by heating and/or pressurization, which may cause liquid leakage due to pinholes. The thickness of the innermost layer may exceed 100 µm. However, if the thickness is increased, the flexibility of the container may be impaired. In addition, this is not preferable in terms of cost.

As a method for laminating each material constituting the sheet member, a known method can be used as a method for manufacturing a normal container. For example, lamination can be performed by coextrusion molding such as multilayer inflation molding and multilayer T die casting, or extrusion lamination in which molten resin is directly laminated, or dry lamination using an adhesive.

In addition, in the case where the amorphous polymer constituting the innermost layer and the resin constituting the base resin layer are laminated by coextrusion molding, they may be laminated directly, but if necessary, in order to sufficiently enhance the adhesion between the base resin layer and the innermost polymer, an adhesive resin represented by "Admer (registered trademark)" manufactured by Mitsui Chemicals Inc., or "Modic (registered trademark)" manufactured by Mitsubishi Chemical Corporation, and the like can also be used. In addition, a composition specified in the specification of Japanese Patent Application No. 2017-140246, which was found by the inventors of the present application and has already applied for a patent, may be used. For example, an adhesive resin containing a resin component composed of linear low density polyethylene, styrene-based elastomer and polypropylene-based resin, in which the ratio of (linear low density polyethylene):(total of styrene-based elastomer and polypropylene resin) ranges from 40:60 to 95:5 by a weight ratio, may be mentioned.

FIG. 1 illustrates a plastic container 10 in which an innermost layer 12a and a base resin layer 12b of a sheet member 12 are directly laminated, and FIG. 2 illustrates a plastic container 20 in which an adhesive resin layer 12c is laminated as an intermediate layer between an innermost layer 12a and a base resin layer 12b of a sheet member 12. The sheet member of the present embodiment may optionally include an intermediate layer, a printed layer, a vapor deposition layer, a coating layer, and the like as layers other than those illustrated.

In the case where the plastic container is a blow molded container, for example, multilayer extrusion blow molding is suitably employed. As a multilayer coextrusion blow molding method, blow molding is carried out by using a multilayer extruder having a plurality of extruders to melt and extrude an amorphous polymer and a crystalline polyolefin resin, and if necessary, an adhesive resin or other synthetic resins by means of the respective extruder thereof, and blowing air. In blow molding, blow molding may be carried out after a preform is once formed. Alternatively, each molten resin layer may be formed into a tubular multilayer parison inside a multilayer parison molding die, and direct blow molding may be performed for blow molding.

A PP-based resin and a PE-based resin are mainly used for the base resin layer constituting the sheet member used in the plastic container of the present embodiment.

The PP-based resin is constituted by, in addition to a homopolymer of propylene, a copolymer obtained by copolymerizing a small amount (preferably 10% by weight or less) of an alpha-olefin such as ethylene and 1-butene, a copolymer produced by multistage polymerization of propylene and alpha-olefin disclosed, for example, in Japanese Unexamined Application, First Publication No. 2001-226435, or the like. In addition, a compound obtained by the aforementioned homopolymers or copolymers, and another polyolefin or resin may also be used. Among these, as a material that relaxes the rigidity of the cyclic polyolefin layer and improves the flexibility of the multilayer film, a material having a relatively flexible grade with a flexural modulus of 400 to 600 MPa, which is widely used for medical containers, is preferably used. In addition, from another viewpoint, the melt flow rate (230° C., 21.2 N) value of the resin constituting the base resin layer preferably ranges from 1 to 4 (g/10 minutes). As a specific example of the resin constituting the base resin layer which can be suitably used in the present embodiment, mention may be made of "Zeras (registered trademark)" (registered trademark) manufactured by Mitsubishi Chemical Corporation. In particular, a PP-based resin having a melting peak temperature ranging from 160 to 170° C. is preferably used.

In addition, as polyethylene used for the base resin layer of the sheet member, a low density polyethylene or a linear low density polyethylene (linear low density polyethylene) is preferably used. The polyethylene mentioned above preferably has a density in the range of 0.880 to 0.920 g/cm$^3$. The alpha-olefin has 12 or less carbon atoms, and as examples thereof, mention may be made of propylene, butene-1, hexene-1,4-methylpentene-1, octene-1, and the like. As the linear low-density polyethylene mentioned above, a product manufactured with a metallocene catalyst is preferable. The linear low-density polyethylene polymerized with a metallocene catalyst exhibits superior transparency and the like because of the reduced structure heterogeneity. In addition, since the molecular weight distribution is uniform, when the linear low-density polyethylene is heated, the polyethylene mentioned above has few bleeds and is less likely to be clouded.

Polypropylene used for the base resin layer or intermediate layer of the sheet member is manufactured by using a Ziegler-Natta catalyst or a metallocene catalyst. Syndiotactic polypropylene produced by using a metallocene catalyst is preferable because superior flexibility and transparency are exhibited. The polypropylene mentioned above preferably has a melting peak temperature of 110° C. or higher, and more preferably 120° C. or higher. When the polypropylene having the temperature properties mentioned above is used for the intermediate layer, heat resistance can be imparted to the plastic container.

The amorphous polymer which is the main component of the innermost layer used in the sheet member of the present embodiment is an amorphous polymer which is composed of at least one type or two or more types of olefin monomers, and at least one type of the olefin monomers is a monomer having a cyclic hydrocarbon skeleton. However, in the case where the amorphous polymer consists of only one type of cyclic olefin monomer (norbornene compound or the like), it may be a ring-opening metathesis polymer such as a norbornene compound, but it is preferable that a single addition polymer such as a norbornene compound or the like be not included.

The amorphous polymer which is the main component of the innermost layer used in the sheet member of the present embodiment includes a copolymer composed of two or more types of cyclic olefin monomers such as norbornene compounds, or an addition polymer obtained by copolymerizing a cyclic olefin monomer and an olefin monomer other than a cyclic olefin monomer such as alpha-olefin, and a polymer obtained by using a cyclic olefin monomer such as a norbornene compound, performing ring-opening metathesis polymerization, and subsequently hydrogenating the remaining double bonds.

As the amorphous polymer which is the main component of the innermost layer used in the sheet member of the present embodiment, the cyclic olefin polymer mentioned above can be used. As examples of such a cyclic olefin polymer, mention may be made of the following materials.

For the production of a cyclic olefin-based polymer, a method in which a ring-opening metathesis polymer of a norbornene is hydrogenated to obtain the cyclic olefin-based polymer, and a method in which a norbornene and an alpha-olefin are subjected to a copolymerization reaction to obtain the cyclic olefin-based polymer are known. The basic structure of the cyclic olefin-based polymer can be expressed as, for example, [chemical formula 2] described in Japanese Unexamined Patent Application, First Publication No. 2011-237572 (refer to Formula (II) shown below). That is, the basic structure thereof is described as a polymer in which cyclic unit skeletons and ethylene unit skeletons are alternately arranged.

[Formula (II)]

(II)

In Formula (II), n is an integer of 1 or more, and $R_1$ and $R_2$ represent a hydrogen atom or an alkyl group, and may be the same or different. $R_1$ and $R_2$ may combine with each other to form a ring. The structure represented by Formula (II) may be a single polymer of one type of cyclic olefin monomer, that is, a homopolymer (in the case of the combination of $R_1$ and $R_2$ bonded to n cyclic unit skeletons being the same). However, the case of a copolymer composed of a plurality of cyclic olefin monomers as shown in [chemical formula 4] of Japanese Unexamined Patent Application, First Publication No. 2014-124927 (refer to Formula (III) shown below), (in the case of the combinations of $R_1$ and $R_2$ bonded to n cyclic unit skeletons being two or more) is also included. Japanese Unexamined Patent Application, First Publication No. 2014-124927 discloses that the chemical structure of "ZEONOR (registered trademark)" 1060 R manufactured by ZEON CORPORATION is expressed as the following Formula (III) (paragraph 0098).

[Formula (III)]

(III)

In Formula (III), m and n are integers of 1 or more, and $R_1$ and $R_2$ represent a hydrogen atom or an alkyl group, and may be the same or different. $R_1$ and $R_2$ may combine with each other to form a ring.

In addition, in the request lecture of the 39th Petroleum and Petrochemical Conference held in 2009 (Session ID: 1C12 "Research on ring-opening metathesis polymerization of cyclic olefins"), it is reported that the main chain structure of "ZEONEX (registered trademark)" and "ZEONOR (registered trademark)" is an atactically controlled random copolymer. In view of this, the production of the cyclic olefin copolymer by the alkene metathesis reaction is industrially carried out and they are easily available by a person having ordinary skill in the art. Even in the plastic container of the present embodiment, the material can be used as an amorphous polymer which is the main component of the innermost layer.

In addition, a copolymer selected from norbornenes and one type of ethylene, propylene, and alpha-olefin is also shown as [chemical formula 1] in Japanese Patent Application No. 2011-237572 mentioned above, and can be represented by the following chemical structure (Formula (IV)).

[Formula (IV)]

(IV)

In Formula (IV), m and n are integers of 1 or more, and $R_1$, $R_2$ and $R_3$ represent a hydrogen atom or an alkyl group, and may be the same or different. In addition, $R_1$ and $R_2$ may be bonded to each other to form a ring. A structure in which $R_1$, $R_2$, and $R_3$ are all hydrogen atoms in Formula (IV) is typically known as "TOPAS (registered trademark)" sold by Polyplastics Co., Ltd., and is introduced in the general catalog of "TOPAS (registered trademark)". The structure in which $R_1$ and $R_2$ are alkyl groups and $R_3$ is a hydrogen atom corresponds to "Apel (registered trademark)" sold by Mitsui Chemicals, Inc., and is described as a typical structure in the product catalog of "Apel (registered trademark)".

These cyclic olefin polymers are resins having superior water vapor barrier properties and are easily available. As described above, in the plastic container of the present embodiment, these cyclic olefin-based polymers can be used as the amorphous polymer which is the main component of the innermost layer, and as the cyclic olefin-based polymer which is the main component of the innermost layer, one type of polymer can be used alone, or two or more types of polymers can be used in combination.

As the cyclic olefin-based polymer, commercially available products as described above can also be used. Although overlapping with the above description, as examples of the commercially available products, mention may be made of ZEONEX (registered trademark) (manufactured by Nippon Zeon Co., Ltd., ring-opening metathesis polymer hydrogenated polymer of norbornene monomer), TOPAS (registered trademark) (manufactured by Polyplastics Co., Ltd., a copolymer of norbornene and ethylene), ZEONOR (registered trademark) (manufactured by Nippon Zeon Co., Ltd., a copolymer based on ring-opening polymerization of dicyclopentadiene and tetracyclopentadodecene), Apel (registered trademark) (manufactured by Mitsui Chemicals, Inc., a copolymer of ethylene and tetracyclododecene), Arton (registered trademark) (manufactured by JSR Corporation, a cyclic olefin resin containing a polar group and using dicyclopentadiene and methacrylic acid ester as raw materials), and the like.

The composition of the material constituting the innermost layer of the sheet member may contain other resin components, in addition to the cyclic olefin polymer. As examples of other resin components, mention may be made of polyolefin-based resins such as polyethylene, polypropylene, polybutene, ethylene/alpha-olefin copolymer, ethylene/(meth)acrylic acid copolymer, ethylene/vinyl acetate copolymer, ethylene/(meth)acrylic acid ester copolymer, and the like, urethane-based resins, rubber-based resins, polyester-based resins, polyester urethane-based resins, acrylic resins, amide-based resins, styrene-based resins, silane-based resins, and the like. By containing these resins, the performance desired for containers such as infusion bag shapes can be improved, such as impact resistance at low temperatures of plastic containers, maintaining of transparency immediately after high-pressure steam sterilization, and improvement of flexibility.

As the material constituting the innermost layer of the sheet member, the material is preferably composed of only a cyclic olefin polymer (that is, contains 100% by mass of the cyclic olefin polymer). In the case of containing other resin components mentioned above, the innermost layer preferably contains a cyclic olefin-based polymer as a main component, that is, in an amount of 50% by mass or more, and particularly preferably in an amount of 70% by mass or more. In the case where the composition ratio of the cyclic olefin-based polymer is low, a trace component or a pharmaceutical ingredient having a high affinity with plastic may be sorbed, and the storage stability of the pharmaceutical ingredient stored in the bag may be insufficient.

The materials constituting the innermost layer of the sheet member may contain various types of additives such as antioxidants, ultraviolet absorbers, antistatic agents, lubricants, antiblocking agents, and the like as long as they do not impair safety or hygiene, in order to improve the appearance of the container, stabilize the quality, and provide other required performance thereto.

The plastic container of the present embodiment, in which a pharmaceutical solution is contained, is subjected to a heat treatment preferably at a temperature of 60° C. or higher, or subjected to a high-pressure steam sterilization at a temperature of over 100° C., and more preferably at a temperature of 121° C. For this reason, in particular, it is very important to design the molecular structure and determine the glass transition temperature so that the molecular motion of the amorphous polymer constituting the innermost layer, that is, the micro-Brownian motion thereof, does not occur. It is necessary to have a glass transition temperature at least equal to or higher than the temperature of heat treatment or high-pressure steam sterilization to which the container is subjected. If the glass transition temperature is lower than the sterilization temperature, the micro-Brownian motion mentioned above occurs during the heat treatment or the high-pressure steam sterilization treatment, and the molecular chain rotates. For this reason, it becomes impossible to prevent sorption or dispersion of the ingredient of the pharmaceutical solution stored in the container. As a result, the amount of active ingredients may be reduced. The optimum glass transition temperature of the amorphous polymer (cyclic polyolefin) which prevents such a phenomenon must be at least equal to or higher than the temperature of the heat treatment or the high-pressure steam sterilization treatment of the container. It is effective that the glass transition temperature of the polymer is 70° C. or higher, preferably 100° C. or higher, and more preferably 130° C. or higher.

In the present embodiment, at least one or more opening parts (ports) for discharging the aqueous solution that is the stored material may be provided in a part of the plastic container. The opening part can be used not only for discharging but also for filling.

With respect to a method for welding the opening part, in the case of the plastic container being a bag-like container, the innermost layers as the sealant layer of the sheet member are superimposed, the port part is inserted between these layers, and subjected to welding by heat sealing.

The port member used in the present embodiment has a tubular shape such as a cylindrical shape, and the base end part is inserted into the opening part of the bag body. Under this state, the port member is tightly bonded to the sheet members on both sides by adhering or heat sealing. The dimension of the port member is not limited in the present invention. For example, if the outer diameter excluding the convex part is about 4 to 20 mm, the wall thickness is about 0.5 to 3 mm, and the length is about 20 to 50 mm, it is suitable as a connection part with an infusion set. In addition, the shape of the port member may be a boat shape or the like at the joint part with the sheet member in order to enhance the joint strength with the bag body.

In addition, after the contents are stored in the bag, the port member is attached with a sealing body (not shown in the drawings) in order to prevent leakage to the outside, prevent dust and bacteria from entering into the system, and maintain the quality of the contents, and then sealed. As the sealing body, an elastic body molded from rubber or elastomer is mainly used. In addition, in order to prevent the sealing body from falling off due to the action of an external force, in general, a cap is attached or a sealing material is arranged as necessary to fix the sealing body.

As a method for manufacturing a port member, a known method can be employed as a method for manufacturing a normal resin molded product, represented by an injection molding method. Different materials may be blended or arranged in multiple layers in order to alleviate the interaction of the contents contained in the plastic container. In order to maximize the effect of the present embodiment, a crystalline polyolefin resin having no cyclic hydrocarbon skeleton, represented by PE or PP, is preferably used as a main component of the port member. In addition, in order to enhance the sealing strength with the cyclic olefin-based resin disposed as the joint surface of the sheet member, for example, a component such as a styrene-based elastomer may be added to the port member within a range that does not impair the heat resistance against the heat treatment. Since the port member of the present embodiment can be easily joined to the cyclic olefin-based resin of the sheet member, the period of time required for sealing can be shortened. Therefore, the superior productivity of the plastic container is exhibited. That is, the plastic container of the present embodiment can be provided at low cost.

As described above, needless to say, it is desirable to use a cyclic olefin-based resin for the innermost layer, in order to prevent the interaction between the contents and the plastic container. However, in the present embodiment, a crystalline polyolefin resin capable of causing the interaction is used as a main component as a port member.

In the present embodiment, the interaction between the contents and the plastic container as a whole is preferably alleviated by setting the content contact portion area occupied by the port member which may cause interaction with the contents to less than a certain ratio with respect to the content contact portion area of the entire plastic container. Therefore, the degree of the interaction between the contents and the plastic container correlates with the size of the content contact area of the plastic container with respect to the volume of the contents to be stored, and appropriate designing is preferably performed.

Using a plastic container which is excessively large relative to the volume of the contents causes not only increase of the interaction, but also increase of the overall size of the package, resulting in reduction of storage efficiency and increase of transport costs. On the other hand, using a plastic container that is tight with respect to the volume of the contents is superior in terms of minimizing the interaction, but it may cause overflow when filling the contents, and there is no "escape" with respect to external force applied during transportation and storage, so that the container may be broken by impact. In particular, in the present embodiment, the cyclic olefin-based resin is used for the innermost layer of the sheet member, and for this reason, the relationship between the appropriate content volume and the dimension of the plastic container (that is, the content contact area) is preferably within a certain range.

More particularly, the relationship between the content contact area $S_B$ (cm$^2$) of the bag body of the plastic container and the content contact area $S_P$ (cm$^2$) of the port member preferably satisfies the following (Expression 1).

$$0.01 \leq S_P/S_B \leq 0.15 \quad \text{(Expression 1)}$$

When the value of $S_P/S_B$ is too large, the interaction with the contents at the content contact portion of the port member may become excessive. When the value of $S_P/S_B$ is small, the interaction with the contents at the content contact portion of the port member does not become excessive, but the size of the port member with respect to the bag body becomes small. For this reason, appropriately designing including opening function and discharging function is preferably carried out.

The area of the content contact part 14 of the bag body 11 corresponds to the inner surface area of the sheet members 15 on both sides facing to the storage part 13, with the proviso that the joint part 11a between the bag body 11 and the port member 15 or the peripheral joint part 11b of the bag body 11 are excluded. In addition, the area of the content contact part 17 of the port member 15 includes a portion communicating with the storage part 13 on the one end 15a side. The content contact parts 14 and 17 are not limited to the parts where the contents are actually in contact, but include parts that can contact the contents by changing the posture of the plastic container.

In addition, the relationship between the volume V (cm$^3$) of the contents stored in the plastic container and the content contact portion area $S_P+S_B$ (cm$^2$) of the entire plastic container is also expressed by, for example, (Expression 2). It is desirable that the ratio be a certain ratio.

$$\alpha < V/(S_P+S_B) < \beta \quad \text{(Expression 2)}$$

Alpha ($\alpha$) and $\beta$ are positive coefficients set appropriately. Preferred ranges defined as $\alpha$ and $\beta$ are $\alpha=0.1$ (cm) and $\beta=0.7$ (cm), more preferably $\alpha=0.15$ (cm) and $\beta=0.6$ (cm).

The plastic container of the present embodiment is a sealable container, and may be in any form as long as it can maintain the sterility of the contents. A container in the form of a blow-molded container such as an infusion bag or a syringe, ampoule or vial generally used in filling and/or storing an injection solution is preferable. In particular, an infusion bag is preferable. In addition, these forms of containers are preferably transparent and non-colored for the purpose of visual confirmation or recognition of the formation and contamination of foreign substances, and particularly insoluble foreign substances. However, in view of the light resistance of the contents, the design of the container, and convenience, it may be colored within a range that does not impair the visual recognition of the contents.

The plastic container of the present embodiment can be manufactured by filling with an aqueous solution containing the aforementioned pyrazolone derivative in the bag with a port (infusion bag, blow molded container, or the like), attaching with an elastic body such as a rubber stopper, and assembling with a cap, and as required, tightly sealing with a sealing cap or an aluminum cap winding. In addition, a plastic container holding sterility can be manufactured by subjecting to a sterilization operation in the arbitrary step during these manufacturing steps. In addition, an operation, such as filtration using a dustproof filter, before filling the contents to these containers, as desired. In the manufacture of the plastic container of the present embodiment, as examples of a specific sterilization method in the sterilization operation, mention may be made of a hot-water immersion sterilization method, a hot-water shower sterilization method, and a high-pressure steam sterilization (autoclave) method.

As described above, the suitable embodiment according to the present invention has been described, but it should be understood that the present invention is not limited to the embodiment. Various shapes, combinations, and the like of the constituent members shown in the embodiments mentioned above are merely examples, and various modifications can be made based on design requirements and the like without departing from the gist of the present invention.

EXAMPLES

Hereinafter, the present invention is described in detail with reference to examples, but the present invention is not limited to the following examples.

Experiment 1:
[Manufacture of Bag Containers for Tests]
<Film Formation of Sheet Member>

A sheet member was formed using a T-die type multilayer film forming machine, by means of a coextrusion method so that an innermost layer had a thickness of 30 (μm) and a total thickness of the sheet member was 250 (μm). In the case where a base resin layer was a PE-based resin, a two-layer sheet in which the base resin layer and the innermost layer were disposed adjacent to each other was formed. In the case where the base resin layer was mainly composed of a PP-based resin, a three-layer configuration was formed in which an adhesive resin layer was disposed between the base resin layer and the innermost layer. The resin compositions used as the base resin layer, the adhesive resin layer, and the innermost layer are listed in Table 1 and Table 2. In Table 1, the numerical value in [ ] represents the thickness of each layer, and the numerical value in ( ) in Table 2 represents the mass ratio of mixing.

TABLE 1

| Test Example No. | Sheet member | | | Port member |
|---|---|---|---|---|
| | Base resin layer | Adhesive resin layer | Innermost layer | |
| 1 | LLDPE1 [220 μm] | — | COP [30 μm] | LLDPE2 |
| 2 | PP [170 μm] | AD [50 μm] | COP [30 μm] | PP-based mixture |

TABLE 1-continued

| Test Example No. | Sheet member | | | Port member |
|---|---|---|---|---|
| | Base resin layer | Adhesive resin layer | Innermost layer | |
| 3 | LLDPE1 [220 μm] | — | COC [30 μm] | LLDPE2 |
| 4 | PP [170 μm] | AD [50 μm] | COC [30 μm] | PP-based mixture |
| 5 | LLDPE1 [220 μm] | — | COP [30 μm] | COP |
| 6 | PP [170 μm] | AD [50 μm] | COP [30 μm] | COP |
| 7 | LLDPE1 [220 μm] | — | COC [30 μm] | COC |
| 8 | PP [170 μm] | AD [50 μm] | COC [30 μm] | COC |
| 9 | LLDPE1 [150 μm] | COP [30 μm] | LLDPE1 [70 μm] | LLDPE2 |
| 10 | LLDPE1 [150 μm] | COC [30 μm] | LLDPE1 [70 μm] | LLDPE2 |
| 11 | LLDPE1 [220 μm] | — | LLDPE1 [30 μm] | LLDPE2 |
| 12 | PP [220 μm] | — | PP [30 μm] | Random PP |

The detailed compositions of "AD (adhesive resin)" used as the adhesive resin layer of the sheet member and "PP-based mixture" of the port member are indicated in Table 2.

TABLE 2

| | Composition |
|---|---|
| AD | PP-based adhesive resin (100) |
| PP-based mixture | Random PP (55) + LLDPE2 (30) + St-based elastomer (15) |

As the materials for forming the sheet members and the port members described in Table 1 and Table 2, the materials described below were used.

LLDPE1: Linear low-density polyethylene (Umerit (registered trademark) 125FN, manufactured by Ube Maruzen Polyethylene Co., Ltd.)

PP: Polypropylene-based thermoplastic elastomer (Zelas (registered trademark) 7025, manufactured by Mitsubishi Chemical Corporation)

COP: Cycloolefin polymer (ZEONOR (registered trademark) 690R, manufactured by Zeon Corporation)

COC: Cycloolefin copolymer (TOPAS (registered trademark) 6013F04, manufactured by Polyplastics Co., Ltd.)

PP adhesive resin: Polypropylene adhesive elastomer (Zelas (registered trademark) MC729, manufactured by Mitsubishi Chemical Corporation)

Random PP: Metallocene-catalyzed polymerized polypropylene (Wintech (registered trademark) WFW4M, manufactured by Japan Polypropylene Corporation)

LLDPE2: Linear low-density polyethylene (Harmolex (registered trademark) NJ744N, manufactured by Japan Polyethylene Co., Ltd.)

St (styrene)-based elastomer: Styrene-ethylene-butylene-styrene block copolymer (Kraton (registered trademark) G (index of styrene contained=13% by mass, specific gravity=0.90 g/cm$^3$, MFR=22 g/10 min (230° C., 5 kgf), manufactured by Kraton Polymers Co., Ltd.)

<Molding of Port Member>

A port member having an inner diameter of the cylindrical part of 15 mm, a height of 38 mm, and a thickness of the cylindrical part of 0.8 mm was obtained by an injection molding method. The resin materials used in each test example are also described in Table 1 and Table 2.

<Manufacture of Bag of Bag Container>

A bag container was manufactured using the sheet member and the port member obtained as described above. The bag container had a size that the inner dimension of the bag body was about 140 (mm)×105 (mm). A port member was sandwiched between two sheets constituting the bag body, and the sheet members and the port member were thermally welded to form a bag container. The area of the liquid contact part (content contact part) of the bag body of the completed bag container was 250 (cm$^2$), and the area of the liquid contact part (content contact part) of the port member was 20 (cm$^2$).

[Stability Evaluation of Contents]

In the container manufactured as described above, the edaravone-containing aqueous solution prepared at pH 3.85 with the composition shown in Table 3 below (composition of edaravone model preparation) was used as the pharmaceutical formulation, and 105 mL thereof was filled in the container. The container was sealed with an isoprene rubber stopper in which the liquid-contacting face was laminated by an ETFE (tetrafluoroethylene-ethylene copolymer) film and a cap formed by the same material as that of each port member.

The container containing the pharmaceutical formulation was subjected to a sterilization treatment for 30 minutes at 105° C. by means of a high-pressure steam sterilizer, and after completion of cooling thereof, the outside of the container was dried to obtain a bag for pharmaceutical formulation. The bag for pharmaceutical formulation which had been subjected to the sterilization operation was placed in a dry laminate outer bag having a three-layer structure of biaxially stretched polyester/aluminum foil/linear low-density polyethylene, together with an oxygen scavenger ("AGELESS (registered trademark)", manufactured by Mitsubishi Gas Chemical Co., Ltd.), and the opening was heat-sealed to complete the preparation of the samples.

TABLE 3

| Component | Amount (mg /100 mL) |
|---|---|
| Edaravone | 30 |
| Sodium chloride | 855 |
| Sodium hydrogen sulfite | 20 |
| L-cysteine hydrochloride hydrate | 10 |
| Sodium hydroxide | appropriate amount |
| Phosphoric acid | appropriate amount |

The prepared bag sample containing the pharmaceutical formulation was allowed to stand for 3 months in an environment of 40° C. and 75% relative humidity, and the aqueous solution of edaravone as the contents was collected from the sample after the storage period, and a residual index of edaravone was measured by means of liquid chromatography under the conditions described below.

Detector: UV absorptiometer (measurement wavelength: 243 nm).

Column: Column for liquid chromatography, in which a stainless steel tube having an inner diameter of 4.6 mm and a length of 150 mm is packed with octadecylsilylated silica gel having a particle diameter of 5 μm.

Column temperature: Constant temperature around 40° C.
Mobile phase: Methanol:water:acetic acid=49.8:49.8:0.4.
Flow rate: 1.0 mL/min.
Injection amount: 20 μL An amount of 3 mL corresponding to about 0.9 mg of edaravone was accurately collected from the test sample bag, and the mobile phase was added thereto so that the total amount was 10 mL. An amount of 1 mL of this solution was accurately measured, and the mobile phase was added thereto so that the total amount was exactly 100 mL. Thereby, a measurement solution was prepared. A test was performed by liquid chromatography on 20 μL of the measurement solution under the test conditions described above. Each peak area was measured by an automatic integration method. The residual index of the edaravone ingredient was determined for each test condition according to the (Equation A) described below. The initial peak area of edaravone was measured in the same procedure as that of the peak area of edaravone after completion of the test after accurately collecting 3 mL from the model pharmaceutical formulation immediately after preparation and before filling the test sample bag.

Residual index of edaravone (%)=100(%)×(Peak area of edaravone at the time of sampling)/ (Peak area of edaravone at the initial value)    (Equation A)

In addition, the same measurement was performed immediately after sterilization, and the influence on the stability of the pharmaceutical formulation due to the sterilization and the influence of storage for a long period of time were considered. It should be noted that the sample in which the residual index of edaravone immediately after sterilization of each sample or after completion of storage for 3 months at 40° C. changed by ±5% or more was determined to be "unsuitable".

Table 4 shows the residual indexes of the component of the edaravone formulations stored in bag containers formed from the sheet members and the port members of Test Examples 1 to 12 having different material compositions. The samples manufactured according to the present invention (Test Examples 1 to 4) exhibit storage stability which is substantially the same as that of the samples (Test Examples 5 to 8) in which the liquid contact parts of the bag container are all formed from a cyclic olefin-based resin. On the other hand, in the samples of Test Example 9 or 10 in which the intermediate layer (adhesive resin layer) of the sheet member contains a cyclic olefin-based resin, but the liquid contact part is all PE, the residual index within ±5% even after storage for 3 months at 40° C. is exhibited. However, it can be clearly seen that the residual index thereof immediately after sterilization remains low, as compared with the present invention. In addition, the samples (Test Example 11 or 12) composed only of PE or PP without using a cyclic olefin-based resin as the sheet material deviate from the standard of the residual index immediately after sterilization. In addition, even in the subsequent storage for 3 months at 40° C., the residual index tends to greatly decrease.

TABLE 4

| Test Example No. | Area of liquid contact part (cm$^2$) | | | Residual index of edaravone (%) | |
| --- | --- | --- | --- | --- | --- |
| | Bag body SB | Port member SP | SP/SB | Immediate after sterilization | After 3 months at 40° C. |
| 1 | 250 | 20 | 0.080 | 99.7 | 99.2 |
| 2 | 250 | 20 | 0.080 | 98.9 | 98.3 |
| 3 | 250 | 20 | 0.080 | 99.1 | 99.6 |
| 4 | 250 | 20 | 0.080 | 99.0 | 99.3 |
| 5 | 250 | 20 | 0.080 | 100.2 | 99.9 |
| 6 | 250 | 20 | 0.080 | 100.9 | 100.3 |
| 7 | 250 | 20 | 0.080 | 99.2 | 99.5 |
| 8 | 250 | 20 | 0.080 | 99.6 | 99.7 |
| 9 | 250 | 20 | 0.080 | 97.6 | 96.7 |
| 10 | 250 | 20 | 0.080 | 98.2 | 97.1 |
| 11 | 250 | 20 | 0.080 | 94.2 | 81.8 |
| 12 | 250 | 20 | 0.080 | 93.5 | 84.5 |

[Table 4]

Experiment 2:

The bag container was manufactured by the sheet member and the port member used in Test Example 1 of Experiment 1. In order to increase the area of the liquid contact part of the port member and enhance the liquid contact part area ratio $S_P/S_B$, the port member in which the dimension in the tubular part height direction was extended and the area of the liquid contact part was 30, 40, or 50 (cm$^2$) was joined. The residual index of edaravone was determined by the same method as that described in Experiment 1. The test results in Experiment 2 are shown in Table 5 together with the test results of Test Example 1 in Experiment 1.

TABLE 5

| Test Example No. | Area of liquid contact part (cm²) | | | Residual index of edaravone (%) | |
| --- | --- | --- | --- | --- | --- |
| | Bag body SB | Port member SP | SP/SB | Immediately after sterilization | After sterilization for 3 months at 40° C. |
| 1 | 250 | 20 | 0.080 | 99.7 | 99.2 |
| 1A | 250 | 30 | 0.120 | 99.3 | 97.4 |
| 1B | 250 | 40 | 0.160 | 99.3 | 94.6 |
| 1C | 250 | 50 | 0.200 | 99.1 | 93.9 |

As the liquid contact area ratio $S_P/S_B$ of the port member increased, the interaction between the pharmaceutical formulation and the bag container increased, and the residual index of edaravone during storage for a long period of time tended to decrease gradually. In addition, in the case where the area of the liquid contact part of the port member was excessively large, the residual index after storage for 3 months at 40° C. was less than 95%. Therefore, it was shown that the area of the liquid contact part of the port member in which the interaction with the contents may occur was required to be designed at a low ratio with respect to the area of the liquid contact part of the bag body.

DESCRIPTION OF SYMBOLS 10, 20 . . . Plastic container,
11 . . . Bag body,
11a . . . Joint part of bag body and port member,
11b . . . Joint part of peripheral of bag body,
12 . . . Sheet member,
12a . . . Innermost layer,
12b . . . Base resin layer,
12c . . . Adhesive resin layer,
13 . . . Storage part,
14 . . . Content contact part of bag body,
15 . . . Port member,
15a . . . One end of port member,
15b . . . other end of port member,
16 . . . opening part,
17 . . . Content contact part of the port member.

What is claimed is:

1. A plastic container comprising: a bag body which is formed into a bag shape by a sheet member and has a storage part on the inside thereof; and at least one tubular port member attached to said bag body, in which one end of the tubular port member communicates with the storage part and an opening part of the other end is exposed outside of the bag body,
wherein said sheet member is formed from two or more layers including a base resin layer and an innermost layer, and said innermost layer is formed from an amorphous polymer, as a main component, formed by polymerizing at least one type or two or more types of olefin monomers, in which at least one type of said olefin monomers is a monomer having a cyclic hydrocarbon skeleton,
wherein said port member is formed from a resin having a crystalline polyolefin having no cyclic hydrocarbon skeleton, as a main component; and
wherein a relationship between a total content contact area $S_B$ (cm²) of said bag body and a total content contact area $S_P$ (cm²) of said port member satisfies the following (Expression 1):

$$0.01 \leq S_P/S_B \leq 0.15 \quad \text{(Expression 1)}.$$

2. The plastic container according to claim 1, wherein said crystalline polyolefin is selected from one or more types of polyethylene, polypropylene, and ethylene/alpha-olefin copolymer.

3. The plastic container according to claim 1, wherein said amorphous polymer has a glass transition temperature of 70° C. or higher.

4. The plastic container according to claim 1, wherein the amorphous polymer has a glass transition temperature of 100° C. or higher.

5. The plastic container according to claim 1, wherein said plastic container is in the form of an infusion bag or a blow molded container.

6. The plastic container according to claim 1, wherein contents stored in said plastic container is a pharmaceutical product.

7. The plastic container according to claim 6, wherein said pharmaceutical product is an aqueous solution containing a pyrazolone derivative or a pharmaceutically acceptable salt thereof.

8. The plastic container according to claim 7, wherein said pyrazolone derivative is 3-methyl-1-phenyl-2-pyrazolin-5-one.

9. The plastic container according to claim 1, wherein the resin having the crystalline polyolefin having no cyclic hydrocarbon skeleton further includes a styrene-based elastomer.

10. The plastic container according to claim 1, wherein the port member has a dimension wherein an outer diameter is 4 to 20 mm, a wall thickness is 0.5 to 3 mm, and a length is 20 to 50 mm.

11. The plastic container according to claim 1, wherein the innermost layer of the sheet member is formed from a cycloolefin polymer or cycloolefin copolymer.

12. The plastic container according to claim 1, wherein the amorphous polymer has a glass transition temperature of 130° C. or higher.

13. The plastic container according to claim 1, wherein a thickness of the sheet member is in a range from 70 to 400 μm, and a thickness of the innermost layer is in a range from 10 to 100 μm.

14. The plastic container according to claim 1, wherein the plastic container is a flexible container which is a soft bag.

15. The plastic container according to claim 1, wherein the plastic container is in the form of a syringe, ampoule or vial.

16. The plastic container according to claim 1, wherein the port member and the innermost layer of the sheet member are welded.

17. The plastic container according to claim 6, wherein the pharmaceutical product includes at least one selected from water and a pharmaceutical solution.

18. The plastic container according to claim 6, wherein a relationship between a volume V (cm$^3$) of the contents stored in the plastic container and a content contact portion area of the plastic container, which is represented by $S_P+S_B$ (cm$^2$), satisfies the following (Expression 2):

$$0.1 < V/(S_P+S_B) < 0.7 \qquad \text{(Expression 2)}.$$

\* \* \* \* \*